United States Patent
Matsuzaki et al.

(10) Patent No.: US 11,745,211 B2
(45) Date of Patent: Sep. 5, 2023

(54) LIQUID EJECTION DEVICE AND LIQUID EJECTION DEVICE CONTROL METHOD

(71) Applicant: Seiko Epson Corporation, Tokyo (JP)

(72) Inventors: Takahiro Matsuzaki, Shiojiri (JP); Hirokazu Sekino, Chino (JP); Hideki Kojima, Matsumoto (JP); Takeshi Seto, Shiojiri (JP); Yuji Saito, Shiojiri (JP)

(73) Assignee: SEIKO EPSON CORPORATION

( * ) Notice: Subject to any disclaimer, the term of this patent is extended or adjusted under 35 U.S.C. 154(b) by 181 days.

(21) Appl. No.: 16/942,967

(22) Filed: Jul. 30, 2020

(65) Prior Publication Data

US 2021/0031225 A1 Feb. 4, 2021

(30) Foreign Application Priority Data

Jul. 31, 2019 (JP) ................................. 2019-140783

(51) Int. Cl.
 B05B 17/06 (2006.01)
 B05B 5/16 (2006.01)

(52) U.S. Cl.
 CPC ............ B05B 17/0607 (2013.01); B05B 5/16 (2013.01)

(58) Field of Classification Search
 CPC ... B05B 17/0646; B05B 17/0607; B05B 5/16; B05B 14/30; B05B 14/00; B05B 5/0533; B05B 17/06; B05B 17/063; A61B 2017/00402; A61B 17/3203
 See application file for complete search history.

(56) References Cited

U.S. PATENT DOCUMENTS

| | | | | |
|---|---|---|---|---|
| 3,526,219 A | * | 9/1970 | Balamuth | A61B 17/320068 433/91 |
| 4,308,546 A | * | 12/1981 | Halasz | B41J 2/025 347/68 |
| 8,794,742 B2 | * | 8/2014 | Yamaguchi | B41J 2/1429 347/44 |
| 2012/0046681 A1 | * | 2/2012 | Kojima | A61B 17/3203 606/167 |
| 2015/0073454 A1 | * | 3/2015 | Uchida | B05B 1/083 606/167 |

FOREIGN PATENT DOCUMENTS

| | | |
|---|---|---|
| CN | 102379736 A | 3/2012 |
| CN | 107051805 A | 8/2017 |
| CN | 207376456 U | 5/2018 |
| JP | 2011-052595 A | 3/2011 |
| JP | 2012-192072 A | 10/2012 |
| JP | 2016-198845 A | 12/2016 |

* cited by examiner

*Primary Examiner* — Christopher R Dandridge
(74) *Attorney, Agent, or Firm* — Harness, Dickey & Pierce, P.L.C.

(57) ABSTRACT

Provided is a liquid ejection device that includes a nozzle that ejects a liquid, a liquid conveying tube that conveys the liquid to the nozzle, an outer tube that is internally provided with the nozzle and the liquid conveying tube, and a first vibration applying unit that applies vibration to the nozzle or the liquid conveying tube. The first vibration applying unit is provided between the nozzle and the outer pipe or between the liquid conveying tube and the outer pipe.

6 Claims, 12 Drawing Sheets

LIQUID EJECTION DEVICE AND LIQUID EJECTION DEVICE CONTROL METHOD

The present application is based on, and claims priority from JP Application Serial Number 2019-140783, filed Jul. 31, 2019, the disclosure of which is hereby incorporated by reference herein in its entirety.

BACKGROUND

1. Technical Field

The present disclosure relates to a liquid ejection device and a liquid ejection device control method.

2. Related Art

A known liquid ejection device performs works such as cleaning, deburring, peeling, trimming, excising, incising, and crushing on a work object by ejecting a pressurized liquid from a nozzle to collide the pressurized liquid with the work object.

For example, JP-A-2016-198845 discloses a high-pressure liquid ejection device that includes a liquid ejecting unit that ejects a liquid, a liquid channel in which the liquid is conveyed to the liquid ejecting unit, a liquid pressurizing mechanism that supplies the liquid to the liquid channel at a high pressure, a temperature adjustment mechanism that adjusts a temperature of the liquid flowing in the liquid channel, and a distance recognizing unit that recognizes a distance from the liquid ejecting unit to a work object. The high-pressure liquid ejection device is configured such that the temperature of the liquid is adjusted according to the distance recognized by the distance recognizing unit.

In addition, JP-A-2016-198845 discloses that a water column shape is disordered and is changed to a droplet shape when bubbles are generated in ejected water, and work efficiency can be maximized by colliding the liquid shape with the work object.

In such a high-pressure liquid ejection device, since droplets can collide with the work object by adjusting the temperature of the liquid according to the distance from the liquid ejecting unit to the work object, the high-pressure liquid ejection device can exhibit high workability.

The temperature adjustment mechanism disclosed in JP-A-2016-198845 includes a heat medium channel that circulates a heat medium, a heat medium temperature adjustment tank that adjusts a temperature of the heat medium, and the like. Since these members occupy a large volume, it is difficult to reduce a size of the high-pressure liquid ejection device. Therefore, a work space of the high-pressure liquid ejection device may be limited.

SUMMARY

A liquid ejection device according to an aspect of the present disclosure includes a nozzle that ejects a liquid, a liquid conveying tube that conveys the liquid to the nozzle, an outer tube that is internally provided with the nozzle and the liquid conveying tube, and a first vibration applying unit that applies vibration to the nozzle or the liquid conveying tube. The first vibration applying unit is provided between the nozzle and the outer tube, or between the liquid conveying tube and the outer tube.

DESCRIPTION OF EXEMPLARY EMBODIMENTS

Hereinafter, preferred embodiments of a liquid ejection device and a liquid ejection device control method according to the present disclosure will be described in detail with reference to the accompanying drawings.

1. First Embodiment

First, a liquid ejection device according to the first embodiment will be described.

Figure 1:
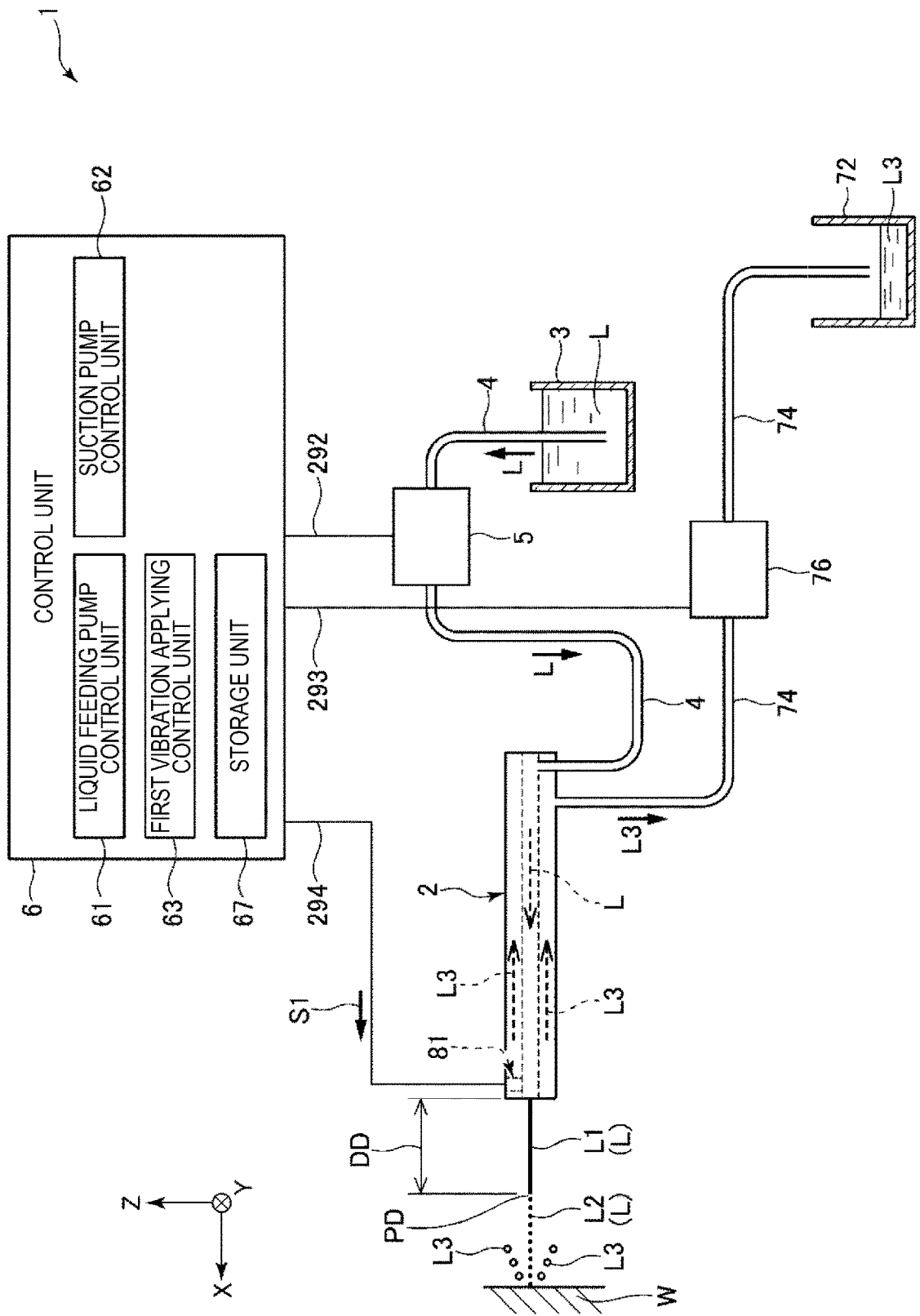
FIG. 1 is a schematic view showing a liquid ejection device according to a first embodiment.
Figure 2:
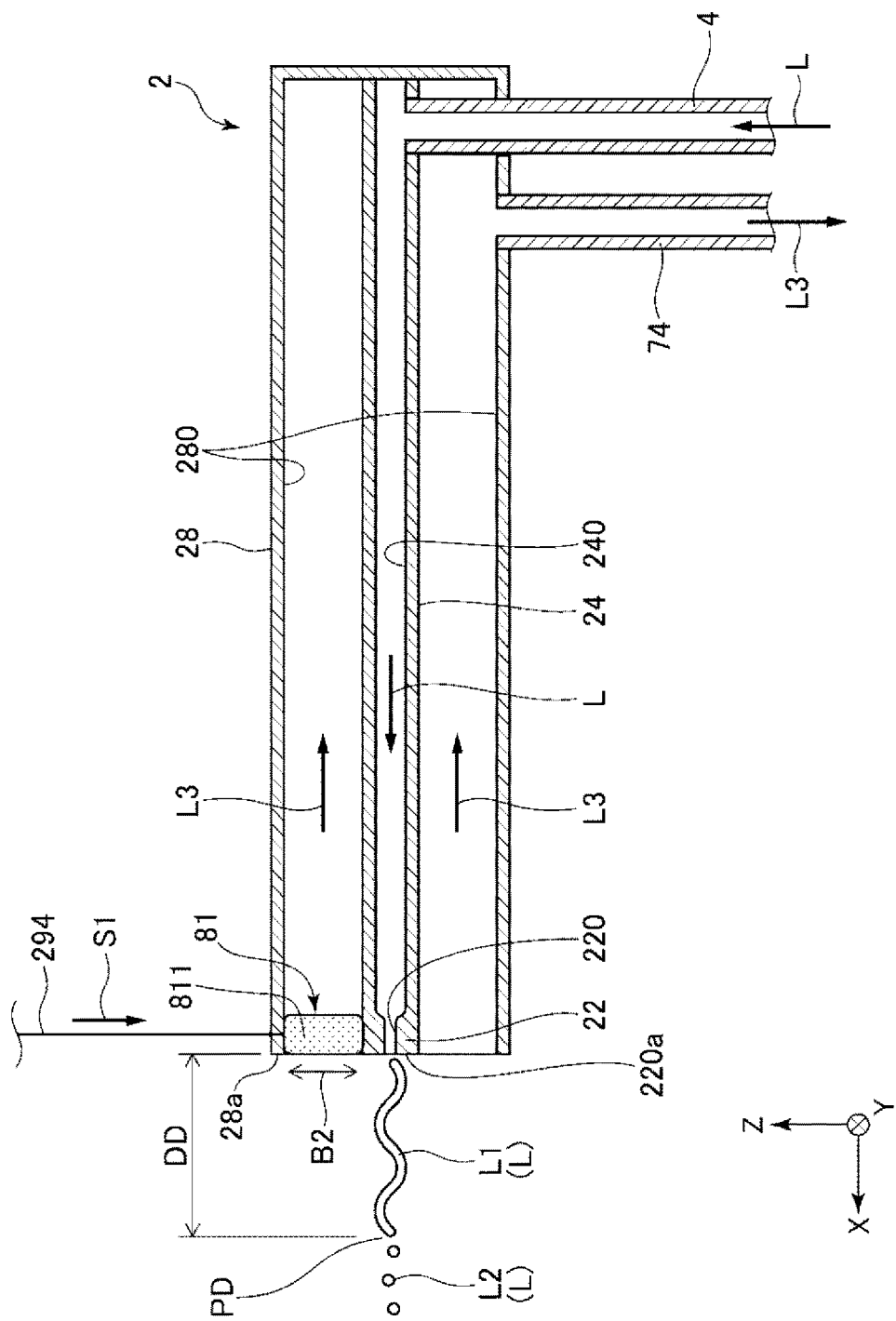
FIG. 2 is a cross-sectional view showing a nozzle unit of the liquid ejection device shown in FIG. 1.
Figure 3:
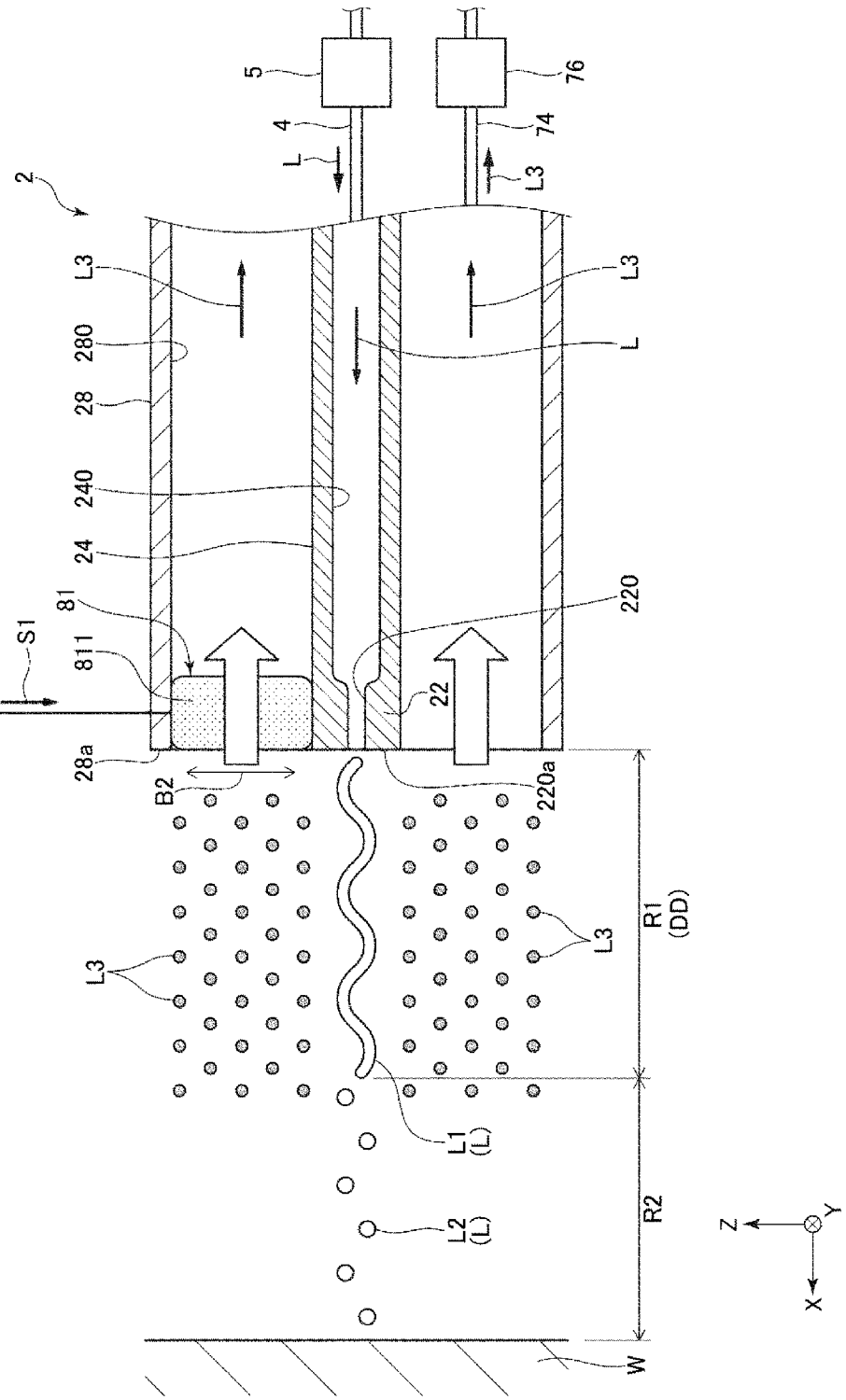
FIG. 3 is a cross-sectional view schematically showing a shape of a liquid ejected from the liquid ejection device shown in FIG. 1.

FIG. 1 is a schematic view showing the liquid ejection device according to the first embodiment. FIG. 2 is a cross-sectional view showing a nozzle unit of the liquid ejection device shown in FIG. 1. FIG. 3 is a cross-sectional view schematically showing a shape of a liquid ejected from the liquid ejection device shown in FIG. 1.

A liquid ejection device 1 shown in FIG. 1 includes a nozzle unit 2, a liquid container 3 that stores a liquid L, a liquid supplying tube 4 that connects the nozzle unit 2 and the liquid container 3, a liquid feeding pump 5, and a control unit 6. The liquid ejection device 1 performs various kinds of works by ejecting the liquid L from the nozzle unit 2 and causing the liquid L to collide the liquid L with a work object W. Examples of the various kinds of works include cleaning, deburring, peeling, trimming, excising, incising, and crushing.

The liquid ejection device 1 shown in FIG. 1 further includes a collection container 72 that stores a discharged liquid L3 suctioned by the nozzle unit 2, a discharged liquid collection tube 74 that connects the nozzle unit 2 and the collection container 72, and a suction pump 76. The liquid L after work is collected as the discharged liquid L3, so that low workability, poor visual field, and the like due to stagnation of the discharged liquid L3 can be prevented.

Hereinafter, each unit of the liquid ejection device 1 will be described in detail.

1.1 Nozzle Unit

As shown in FIG. 2, the nozzle unit 2 includes a nozzle 22, a liquid conveying tube 24, and a suction tube 28. The nozzle 22 ejects the liquid L towards the work object W shown in FIG. 1. The liquid conveying tube 24 conveys the liquid L to the nozzle 22.

For the convenience of description, an axis connecting the nozzle 22 and the work object W is defined as an X axis, and an axis that is orthogonal to the X axis and is an axis of the liquid supplying tube 4 in the vicinity of a connection portion between the liquid conveying tube 24 and the liquid supplying tube 4 is defined as a Z axis in the drawings of the present application. An axis orthogonal to both the X axis and the Z axis is defined as a Y axis. On the X axis, a direction from the nozzle 22 towards the work object W is defined as an "X axis positive side" or a "tip end side", and an opposite direction is defined as an "X axis negative side" or a "base end side". On the Z axis, a direction from the liquid supplying tube 4 towards the liquid conveying tube 24 is defined as a "Z axis positive side", and an opposite direction is defined as a "Z axis negative side".

Hereinafter, each part of the nozzle unit 2 will be described in detail.

The nozzle 22 is attached to a tip end portion of the liquid conveying tube 24. The nozzle 22 is internally provided with a nozzle channel 220 through which the liquid L passes. An inner diameter of the tip end portion of the nozzle channel 220 is smaller than an inner diameter of a base end portion of the nozzle channel 220. The liquid L conveyed towards the nozzle 22 in the liquid conveying tube 24 is formed into a stream through the nozzle channel 220 and is ejected. The nozzle 22 shown in FIG. 2 may be a member separate from the liquid conveying tube 24, or may be integrally formed with the liquid conveying tube 24.

The liquid conveying tube 24 is a tube that connects the nozzle 22 and the liquid supplying tube 4, and includes a liquid channel 240 that conveys the liquid L in the liquid conveying tube 24. The above-described nozzle channel 220 communicates with the liquid supplying tube 4 through the liquid channel 240. The liquid conveying tube 24 may be a straight tube, or all or a part of the liquid conveying tube 24 may be a curved tube. The liquid conveying tube 24 may include a portion whose inner diameter changes.

The nozzle 22 and the liquid conveying tube 24 may have rigidity to an extent that the nozzle 22 and the liquid conveying tube 24 do not deform when the liquid L is ejected. A constituent material of the nozzle 22 includes, for example, a metal material, a ceramic material, and a resin material. A constituent material of the liquid conveying tube 24 includes, for example, a metal material, and a resin material. The liquid conveying tube 24 is preferably made of a metal material.

An inner diameter of the nozzle channel 220 is appropriately selected according to a work content, a material of the work object W, and the like. For example, the inner diameter of the nozzle channel 220 is preferably 0.05 mm or more and 1.0 mm or less, and more preferably 0.10 mm or more and 0.30 mm or less.

As described above, the liquid L conveyed towards the nozzle 22 in the liquid conveying tube 24 is formed into a stream through the nozzle channel 220, and is ejected. The liquid L ejected from the nozzle 22 flies for a predetermined distance as a continuous columnar ejected flow L1. In the present embodiment, since the nozzle 22 is vibrated by a first vibration applying unit 81 to be described later, the ejected flow L1 flies while being changed to a shape such as a waveform. Thereafter, the ejected flow L1 is changed to droplets L2. Then, the droplets L2 collide with the work object W, and the work can be performed by using an erosion effect of the droplets L2, that is, a so-called water hammer phenomenon.

A position where the ejected flow L1 is changed to the droplets L2 is referred to as a droplet forming position PD. A distance from a nozzle opening 220a to the droplet forming position PD is referred to as a droplet forming distance DD.

As shown in FIG. 2, the nozzle unit 2 includes the suction tube 28 that is an outer tube of the liquid conveying tube 24. The suction tube 28 is provided to surround the nozzle 22 and an outer peripheral surface of the liquid conveying tube 24. A position of an opening 28a of the suction tube 28 along the X axis coincides with the nozzle opening 220a of the nozzle 22. Accordingly, the nozzle 22 and the liquid conveying tube 24 are inserted into a suction channel 280 of the suction tube 28.

The position of the opening 28a along the X axis and a position of the nozzle opening 220a may not coincide with each other. For example, the nozzle opening 220a may protrude with respect to the opening 28a towards the X axis positive side. In contrast, the nozzle opening 220a may be backward with respect to the opening 28a at the X axis negative side.

As described above, the suction tube 28 is internally provided with the suction channel 280 that can suction a liquid. The suction channel 280 communicates with an internal channel of the discharged liquid collection tube 74 provided at a base end side of the suction channel 280. The suction channel 280 suctions a liquid by a suction pump 76 through the discharged liquid collection tube 74.

Such a suction tube 28 is provided, so that the discharged liquid L3 such as a reflected liquid flow and a suctioned liquid flow can be prevented from stagnating in the vicinity of the work object W. If the discharged liquid L3 stagnates in the vicinity of the work object W, newly flying droplets L2 collide with the discharged liquid L3. In this case, a colliding pressure from the droplets L2 cannot be applied to the work object W, and work efficiency is lowered. Therefore, the discharged liquid L3 is suctioned to prevent the work efficiency from lowering. In addition, a poor visual field due to scattering of the discharged liquid L3 is prevented, so that the work efficiency can be prevented from lowering.

From this viewpoint, an internal pressure of the suction tube 28 that is an outer tube, that is, a pressure of the suction channel 280 is lower than an atmospheric pressure. Accordingly, the discharged liquid L3 can be suctioned based on a difference between the pressure of the suction channel 280 and the atmospheric pressure. Therefore, low work efficiency due to scattering of the discharged liquid L3 can be prevented.

The reflected liquid flow refers to a liquid flow or droplets generated by colliding the ejected liquid L with the work object W and reflecting the ejected liquid L. The suction liquid flow refers to a liquid flow or droplets generated by drawing the reflected liquid flow or the like accompanied by suctioning performed by the suction tube 28.

An inner diameter of the suction channel 280 is preferably 2 times or more and 20 times or less, and more preferably 3 times or more and 15 times or less of an outer diameter of the nozzle 22 or the liquid conveying tube 24. Accordingly, an appropriate gap is formed between the nozzle 22 and the suction tube 28 or between the liquid conveying tube 24 and the suction tube 28. As a result, even if the discharged liquid L3 contains residues or the like after work, the suction channel 280 can be prevented from being stuck. A pressure reducing speed can be necessarily and sufficiently ensured. Therefore, the discharged liquid L3 in the suction channel 280 can be quickly suctioned, and the discharged liquid L3 can be more reliably prevented from stagnating in the vicinity of the work object W.

The outer diameters of the nozzle 22 and the liquid conveying tube 24 are appropriately set according to a work content, a material of the work object W, and the like. For example, the outer diameters of the nozzle 22 and the liquid conveying tube 4 are each preferably 1.0 mm or more and 10.0 mm or less, and more preferably 2.0 mm or more and 6.0 mm or less. The outer diameter of the nozzle 22 or the liquid conveying tube 24 refers to the larger one between the outer diameter of the nozzle 22 and the outer diameter of the liquid conveying tube 24.

The suction tube 28 may have rigidity to an extent that the suction tube 28 does not deform when the suction channel 280 is depressurized. A constituent material of the suction tube 28 includes, for example, a metal material, a ceramic material, a glass material, and a resin material. Among these materials, the suction tube 28 is preferably made of a metal material or a ceramic material particularly from the viewpoint of having sufficient rigidity. The suction tube 28 may be a straight tube or a curved tube.

The suction tube 28 may be opaque, translucent, or transparent. When the suction tube 28 is translucent or transparent, it is easy to visually confirm the liquid L ejected from the nozzle 22, the discharged liquid L3, and the like. As a result, position accuracy for the work can be improved.

The outer tube of the liquid conveying tube 24 is the suction tube 28 having a function of suctioning the discharged liquid L3 in the present embodiment. Alternatively, the outer tube may have a function other than suctioning the discharged liquid L3. For example, the outer tube may have a function of generating an airflow to blow off the discharged liquid L3 by increasing a pressure of an internal channel of the outer tube to be higher than the atmospheric pressure.

Here, the liquid L ejected from the nozzle 22 of the liquid ejection device 1 flies in the air and collides with the work object W. The work can be performed on the work object W with a colliding pressure at this time.

The liquid L ejected from the nozzle 22 flies as the continuous columnar ejected flow L1 immediately after the ejection. As shown in FIG. 3, such a continuous ejected flow L1 is generated in a region having a predetermined distance from a tip end of the nozzle 22. This region is referred to as a "continuous flow region R1". On the other hand, a shape of the continuous ejected flow L1 is disordered and the ejected flow L1 is changed to the droplets L2 at a side closer to the work object W than the continuous flow region R1. A region where the droplets L2 are generated is referred to as a "droplet flow region R2". When the droplets L2 generated in such a manner collides with the work object W, a colliding pressure can be increased even at a same flow rate as compared with a case in which the ejected flow L1 collides with the work object W. As a result, the work efficiency can be improved.

In order to improve handleability of the liquid ejection device 1, it is required to shorten a length of the continuous flow region R1, that is, the above-described droplet forming distance DD. Even a distance between the nozzle unit 2 and the work object W is shortened by shortening the droplet forming distance DD, the droplets L2 can collide with the work object W. As a result, it is easy to know a positional relationship between the work object W and the nozzle unit 2 and the workability can be improved without lowering the work efficiency.

As shown in FIG. 2, the nozzle unit 2 includes the first vibration applying unit 81 that applies vibration to the nozzle 22. In particular, the first vibration applying unit 81 is provided between the nozzle 22 and the suction tube 28 in FIG. 2. The first vibration applying unit 81 may be any type as long as the first vibration applying unit 81 can apply vibration to the nozzle 22 with respect to the suction tube 28. A vibration direction is not particularly limited, and may be a direction along the X axis or a direction having a component intersecting the X axis, for example, a direction along the Z axis or the Y axis. When the vibration direction is along the direction having a component intersecting the X axis, the vibration can be efficiently applied to the ejected flow L1 ejected from the nozzle 22. As a result, the ejected flow L1 can be vibrated in a direction intersecting the X axis that is a flying direction as shown in FIG. 2. That is, the ejected flow L1 flies while exhibiting a waveform as shown in FIG. 2.

The ejected flow L1 can be changed to the droplets L2 in a shorter time by applying such vibration. Therefore, the droplet forming distance DD can be further shortened, and the workability can be improved.

Since the first vibration applying unit 81 can apply vibration to the nozzle 22 or the liquid conveying tube 24 which will be described later, it is likely to achieve a relatively small size. Therefore, even if the first vibration applying unit 81 is provided between the nozzle 22 and the suction tube 28, it is less likely to increase the size of the nozzle unit 2. As a result, the liquid ejection device 1 having a small size and good portability can be implemented. In particular, restrictions on a work environment can be reduced by reducing the size of the nozzle unit 2. Accordingly, the workable liquid ejection device 1 can be implemented even at a work site where a work space is limited such as a work in a tube. In addition, the nozzle unit 2 can have a small size and a light weight. Therefore, the portability of the nozzle unit 2 can be improved.

The first vibration applying unit 81 according to the present embodiment includes a piezoelectric element 811. A wire 294 is drawn out from the piezoelectric element 811 via the suction tube 28. The piezoelectric element 811 is electrically coupled to the control unit 6 via the wire 294. The piezoelectric element 811 vibrates so as to repeatedly expand and contract along the Z axis, based on an inverse piezoelectric effect, according to a first drive signal S1 output from the control unit 6.

A vibration pattern of the piezoelectric element 811 may be a periodic pattern or a non-periodic pattern as long as it is a vibration pattern that can displace the nozzle 22 in any direction. When the vibration pattern is a periodic pattern, a frequency of the variation pattern may be constant or variable. The piezoelectric element 811 may be an element that expands and contracts along the Z axis as shown in FIG. 2, or may be an element that expands and contracts along the X axis or the Y axis. The piezoelectric element 811 may be a flexural vibration element.

The piezoelectric element 811 includes, for example, a piezoelectric body and an electrode provided on the piezoelectric body. Examples of a constituent material of the piezoelectric body include piezoelectric ceramics such as lead zirconate titanate (PZT), barium titanate, lead titanate, potassium niobate, lithium niobate, lithium tantalate, sodium tungstate, zinc oxide, barium strontium titanate (BST), strontium bismuth tantalate (SBT), lead metaniobate, and lead scandium niobate.

The piezoelectric element 811 may be replaced with any element or mechanical element that can displace the nozzle 22 in any direction. Examples of such an element or mechanical element include a magnetostrictive element, an electromagnetic actuator, and a combination of a motor and a cam.

The piezoelectric element 811 may be in contact with an inner surface of the suction tube 28, and is preferably fixed to the inner surface of the suction tube 28. Accordingly, since slippage between the suction tube 28 and the piezoelectric element 811 is prevented, the nozzle 22 can be vibrated efficiently.

On the other hand, the piezoelectric element 811 may be in contact with an outer surface of the nozzle 22, and is preferably fixed to the outer surface of the nozzle 22. Accordingly, even when the liquid conveying tube 24 has no elasticity, the nozzle 22 can be efficiently vibrated at a target vibration pattern.

Various kinds of adhesive materials such as an adhesive, a solder, and a brazing material can be used to fix the piezoelectric element 811.

Although the first vibration applying unit 81 shown in FIG. 2 is provided between the nozzle 22 and the suction tube 28, the first vibration applying unit 81 may be provided between the liquid conveying tube 24 and the suction tube 28.

Figure 4:
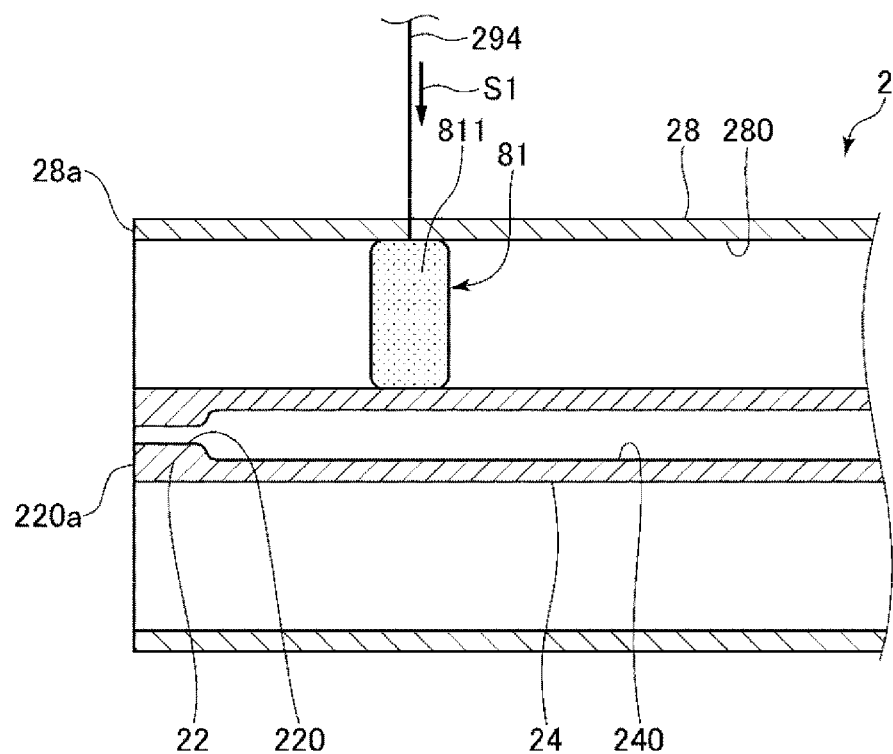
FIG. 4 is a cross-sectional view schematically showing a modification of the nozzle unit shown in FIG. 3.

FIG. 4 is a cross-sectional view schematically showing a modification of the nozzle unit shown in FIG. 3.

Hereinafter, a nozzle unit according to the modification will be described. In the following description, differences from the nozzle unit 2 shown in FIG. 3 will be mainly described, and descriptions of the same matters will be omitted.

The nozzle unit 2 shown in FIG. 4 is similar to the nozzle unit 2 shown in FIG. 3 except that a position of the first vibration applying unit 81 is different.

Specifically, the first vibration applying unit 81 shown in FIG. 3 described above is provided between the nozzle 22 and the suction tube 28 while the first vibration applying unit 81 shown in FIG. 4 is provided between the liquid conveying tube 24 and the suction tube 28. In such a case, the first vibration applying unit 81 can apply vibration to the liquid conveying tube 24. As a result, the vibration can be applied to the ejected flow L1 ejected from the nozzle 22, and the ejected flow L1 can be changed to the droplets L2 in a short time.

The position of the first vibration applying unit 81 in the entire length of the liquid conveying tube 24 is not particularly limited, and may be at a tip end side or other positions.

1.2 Liquid Container

The liquid container 3 stores the liquid L. The liquid L stored in the liquid container 3 is supplied to the nozzle unit 2 via the liquid supplying tube 4.

The liquid L is preferably water, and may be an organic solvent or the like. Any solute may be dissolved in the water or the organic solvent, and any dispersoid may be dispersed in the water or the organic solvent.

The liquid container 3 may be a closed container or an open container.

1.3 Liquid Feeding Pump

The liquid feeding pump 5 is provided in the middle or an end portion of the liquid supplying tube 4. The liquid L stored in the liquid container 3 is suctioned by the liquid feeding pump 5 and supplied to the nozzle unit 2 at a predetermined pressure.

The control unit 6 to be described later is electrically coupled to the liquid feeding pump 5 via a wire 292. The liquid feeding pump 5 has a function of changing a pressure of the supplied liquid L based on a drive signal output from the control unit 6.

1.4 Collection Container

The discharged liquid L3 suctioned by the suction tube 28 described above is sent to the collection container via the discharged liquid collection tube 74. The collection container 72 stores the discharged liquid L3.

1.5 Suction Pump

The suction pump 76 is provided in the middle or an end portion of the discharged liquid collection tube 74. The discharged liquid L3 can be suctioned and sent to the collection container 72 by depressurizing the suction channel 280 by the suction pump 76.

The control unit 6 to be described later is electrically coupled to the suction pump 76 via a wire 293. The suction pump 76 has a function of changing a pressure of the suction channel 280 based on a drive signal output from the control unit 6.

1.6 Control Unit

The control unit 6 is electrically coupled to the nozzle unit 2 via the wire 294. The control unit 6 is electrically coupled to the liquid feeding pump 5 and the suction pump 76 via the wire 292 and the wire 293.

The control unit 6 shown in FIG. 1 includes a liquid feeding pump control unit 61, a suction pump control unit 62, a first vibration applying control unit 63, and a storage unit 67.

The liquid feeding pump control unit 61 outputs a drive signal to the liquid feeding pump 5. Drive of the liquid feeding pump 5 is controlled by the drive signal. Accordingly, the liquid L can be supplied to the nozzle unit 2 at a predetermined pressure, a predetermined drive time, and the like.

The suction pump control unit 62 outputs a drive signal to the suction pump 76. Drive of the suction pump 76 is controlled by the drive signal. Accordingly, the suction pump 76 can be driven at a predetermined pressure, a predetermined drive time, and the like, and a suction speed and suction time of the discharged liquid L3 suctioned by the suction tube 28 can be adjusted.

The first vibration applying control unit 63 outputs the first drive signal S1 to the first vibration applying unit 81. Drive of the piezoelectric element 811 is controlled by the first drive signal S1. Accordingly, the piezoelectric element 811 can be driven at a predetermined frequency, a predetermined amplitude, and the like, and a frequency and an amplitude of the vibration applied to the ejected flow L1 can be adjusted. As a result, the droplet forming distance DD in which the ejected flow L1 is changed into the droplets L2 can be adjusted.

The control unit 6 can control two or more of the drive of the liquid feeding pump 5, the drive of the suction pump 76, and the drive of the first vibration applying unit 81 in cooperation with each other.

Functions of the control unit 6 are implemented by hardware such as an arithmetic unit, a memory, and an external interface.

Examples of the arithmetic unit include a central processing unit (CPU), a digital signal processor (DSP), and an application specific integrated circuit (ASIC).

Examples of the memory include a read only memory (ROM), a flash ROM, a random access memory (RAM), and a hard disk.

1.7 Operation of Liquid Ejection Device

Next, an operation of the liquid ejection device 1 will be described.

The liquid L stored in the liquid container 3 is suctioned by the liquid feeding pump 5 and ejected through the liquid supplying tube 4, the liquid channel 240, and the nozzle channel 220. At this time, the first vibration applying unit 81 applies vibration to the nozzle 22 or the liquid conveying tube 24. Accordingly, the vibration is applied to the ejected flow L1 ejected from the nozzle 22. As a result, the ejected flow L1 can be changed to the droplets L2 in a short time, and the droplet forming distance DD can be shortened.

As shown in FIG. 3, the liquid L ejected from the liquid ejection device 1 flies as the continuous columnar ejected flow L1 immediately after the ejection. At this time, since the piezoelectric element 811 of the first vibration applying unit 81 vibrates vertically along a vibration axis B2 shown in FIG. 3, the nozzle 22 also vibrates along the Z axis accordingly. Then, the ejected flow L1 flies while being vibrated in a wave shape having an amplitude along the Z axis. As a result, the ejected flow L1 is changed to the droplets L2 in a shorter time than the related art. That is, the droplet forming distance DD can be shortened. As a result, the droplets L2 can collide with the work object W even when the distance from the nozzle opening 220*a* to the work object W is short, so that the work efficiency can be improved.

The distance from the nozzle opening 220*a* to the work object W is also referred to as a standoff distance. If the standoff distance can be shortened without lowering the work efficiency, an operator can easily know a work position. Therefore, the workability can be improved, and the work efficiency can also be increased from this viewpoint.

As described above, the liquid ejection device 1 according to the present embodiment includes the nozzle 22 that ejects the liquid L, the liquid conveying tube 24 that conveys the liquid L to the nozzle 22, the suction tube 28 that is an outer tube and is internally provided with the nozzle 22 and the liquid conveying tube 24, and the first vibration applying unit 81 that applies vibration to the nozzle 22 or the liquid conveying tube 24.

According to such a liquid ejection device 1, the liquid L can be vibrated and ejected, that is, can be ejected as the ejected flow L1 deformed into a nonlinear shape. Accordingly, the droplet forming distance DD can be shortened. In addition, since the first vibration applying unit 81 may apply vibration to the nozzle 22 or the liquid conveying tube 24, it is easy to reduce the size of the liquid ejection device 1. Therefore, the liquid ejection device 1 having a small size and good portability can be implemented. Such a liquid ejection device 1 is also useful at a work site where a work space is limited.

In the present embodiment, in particular, the first vibration applying unit 81 is provided between the nozzle 22 and the suction tube 28 or between the liquid conveying tube 24 and the suction tube 28. Accordingly, the first vibration applying unit 81 can be accommodated inside the suction tube 28. Therefore, a protruding portion from the nozzle unit 2 can be reduced, and the size of the nozzle unit 2 is reduced and operability is improved. When the first vibration applying unit 81 expands and contracts along the Z axis or the like, an expansion and contraction amount thereof can be used for displacement of the nozzle 22 or the liquid conveying tube 24. Accordingly, a sufficient displacement amount of the nozzle 22 can be ensured without increasing the size of the first vibration applying unit 81.

The related art discloses a technique for controlling droplet formation by adjusting a temperature of a liquid to be ejected. This technique has a problem that the temperature of the liquid is affected by an outside temperature. Therefore, there is a problem that the droplet forming distance is affected by the outside temperature and it is difficult to control the droplet forming distance to a target distance.

In contrast, according to the present embodiment, the droplet forming distance DD can be shortened without being affected by the outside temperature. Therefore, the liquid ejection device 1 having good handleability can be implemented.

A colliding range in which the droplets L2 collide with the work object W can be expanded to a wide range by vibrating and ejecting the liquid L. As a result, a work region can be easily expanded to improve the work efficiency.

A drive frequency of the first vibration applying unit 81 is not particularly limited, and is preferably 0.01 kHz or more and 50 kHz or less, and more preferably 0.5 kHz or more and 30 kHz or less. Accordingly, the droplet forming distance DD can be further shortened, and the droplets L2 can be generated more stably.

A voltage of the first drive signal S1 input into the first vibration applying unit 81 slightly varies depending on a configuration of the piezoelectric element 811, and is preferably 1 V or more and 100 V or less. Accordingly, since the piezoelectric element 811 vibrates at a necessary and sufficient amplitude, the droplets L2 can be generated more stably.

A waveform of the first drive signal S1 input into the first vibration applying unit 81 may be a periodic waveform such as a sine wave, a rectangular wave, and a sawtooth wave, a non-periodic waveform, or the like.

Figure 5:
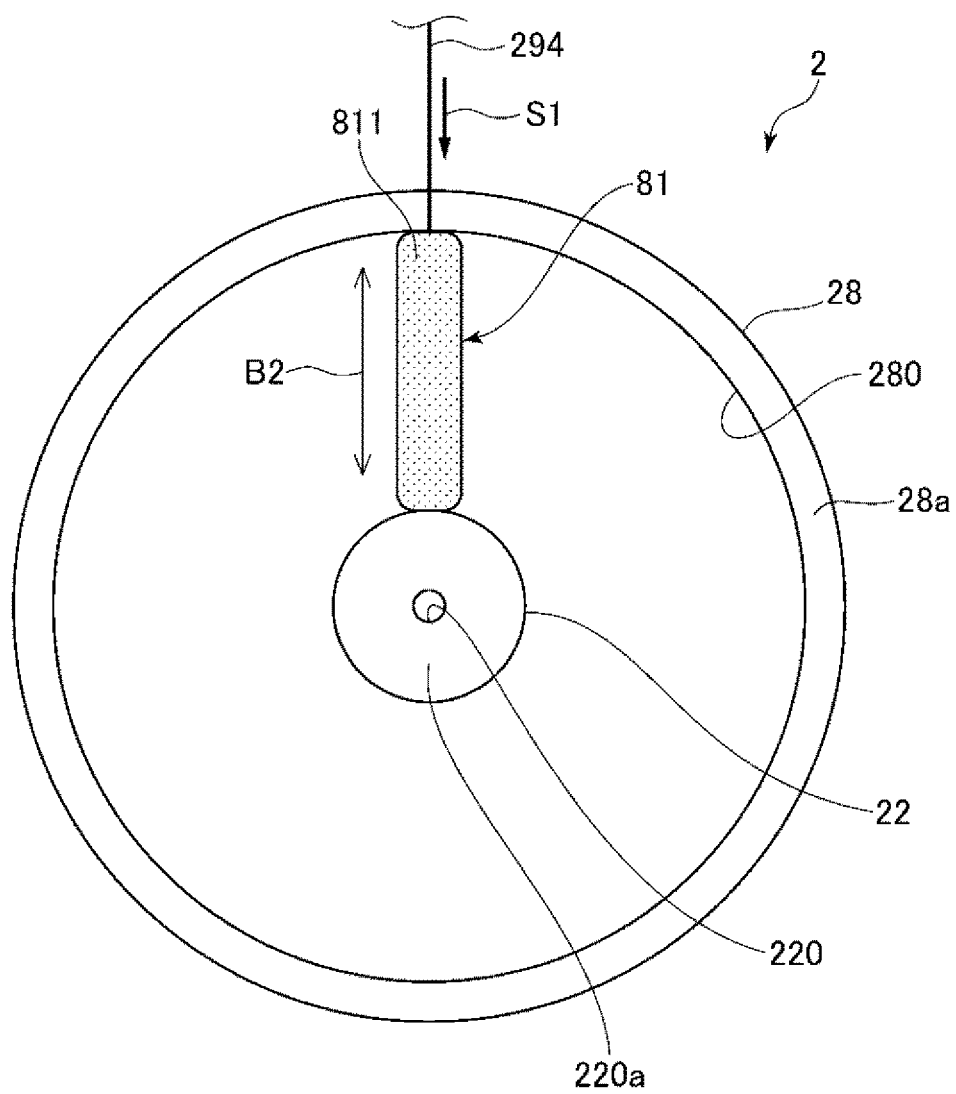
FIG. 5 is a view showing the nozzle unit shown in FIG. 3 as viewed from a tip end side.

FIG. 5 is a view showing the nozzle unit 2 shown in FIG. 3 as viewed from a tip end side.

The suction tube 28 and the nozzle 22 shown in FIG. 5 are arranged concentrically with each other as viewed from the tip end side. Accordingly, the suction channel 280 is arranged to surround the nozzle 22 when the nozzle unit 2 is viewed from the tip end side. Therefore, the discharged liquid L3 can be suctioned in a space surrounding a flying path of the droplets L2. As a result, a clearance is ensured in the flying path of the droplets L2, the discharged liquid L3 is less likely to enter the flying path, and the droplets L2 can stably collide with the work object W.

An arrangement of the suction tube 28 and the nozzle 22 is not limited to the arrangement shown in FIG. 5, and the suction tube 28 and the nozzle 22 may be non-concentrically arranged.

2. Second Embodiment

Next, a liquid ejection device according to the second embodiment will be described.

Figure 6:
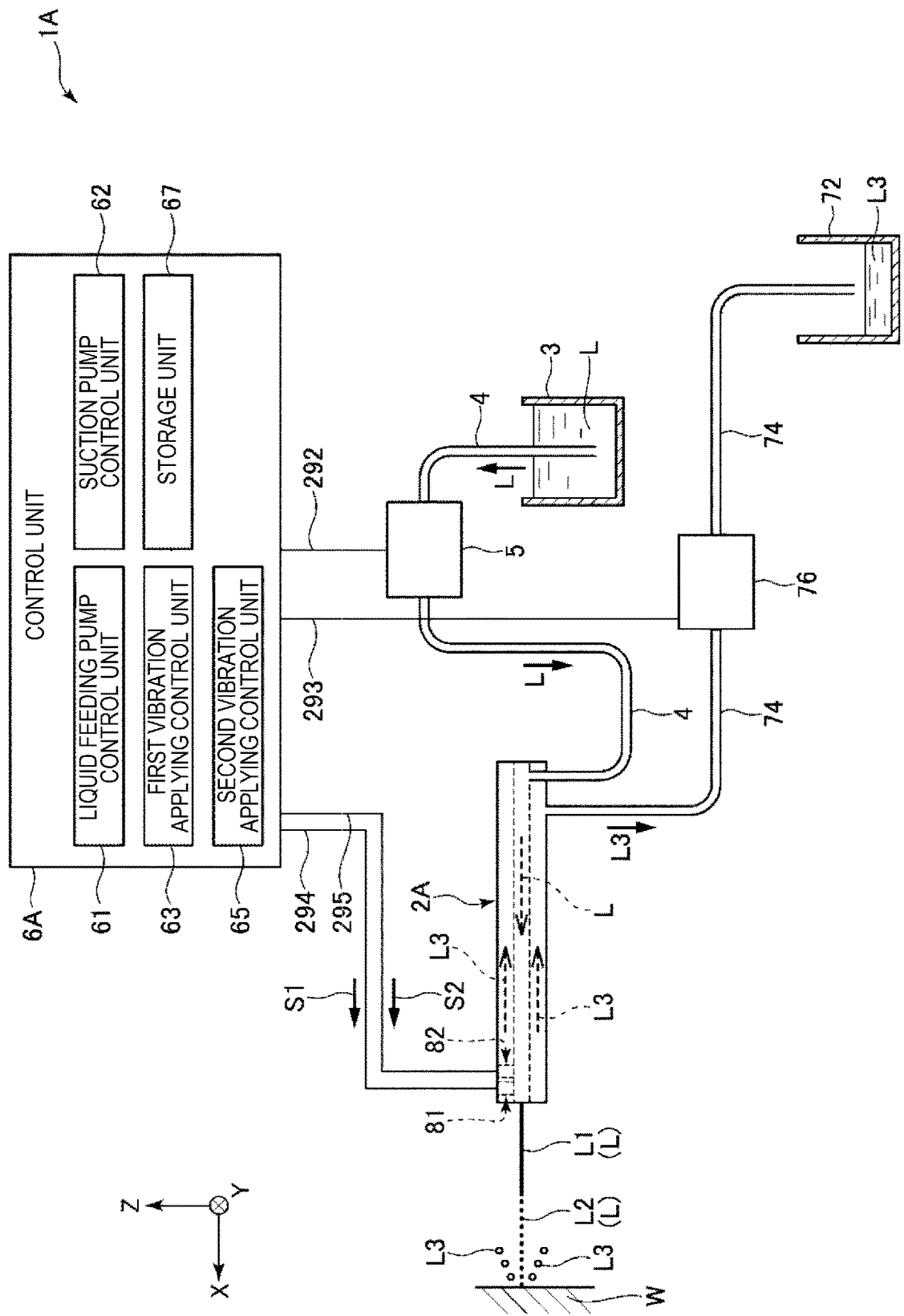
FIG. 6 is a schematic view showing a liquid ejection device according to a second embodiment.
Figure 7:
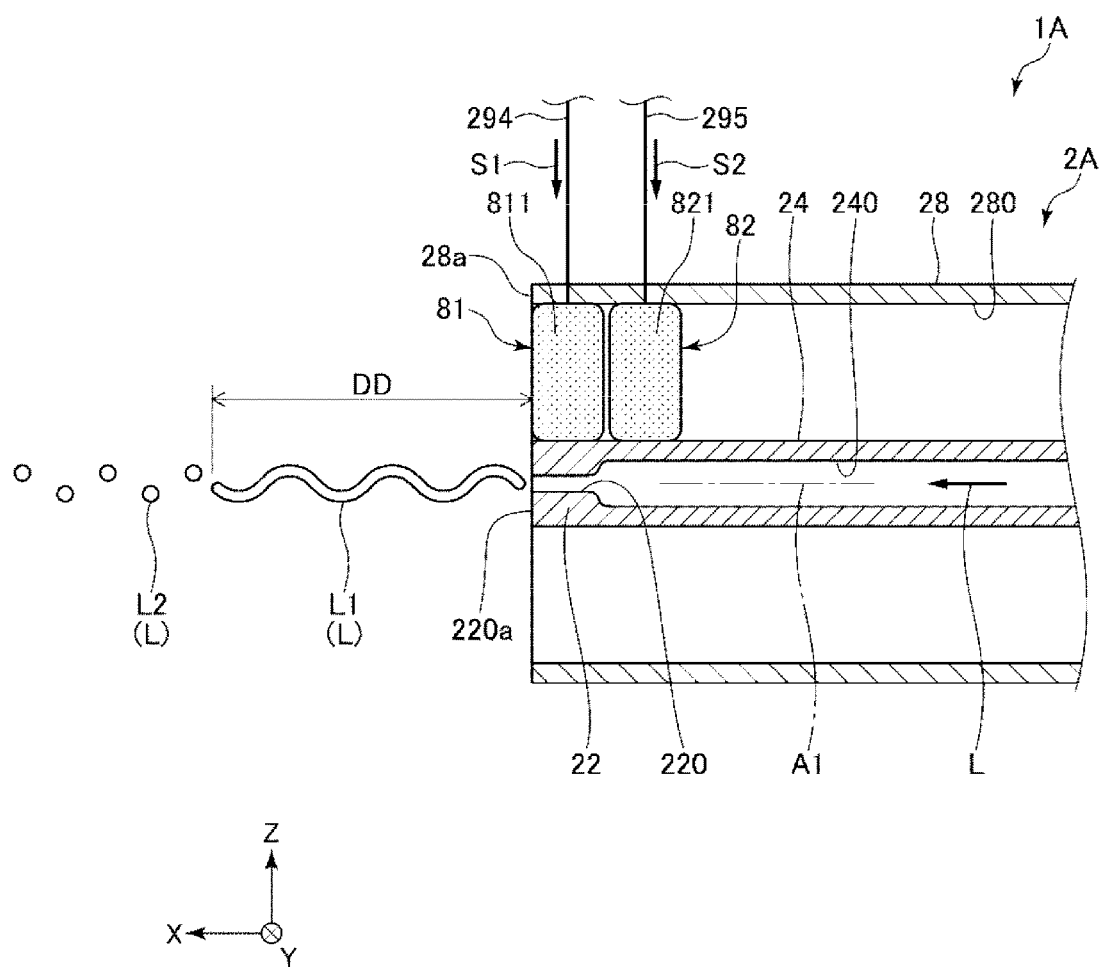
FIG. 7 is a cross-sectional view showing a nozzle unit shown in FIG. 6.

FIG. 6 is a schematic view showing the liquid ejection device according to the second embodiment. FIG. 7 is a cross-sectional view showing a nozzle unit shown in FIG. 6.

Hereinafter, the second embodiment will be described, differences from the first embodiment will be mainly described in the following description, and descriptions of the same matters will be omitted. In FIG. 6, the same components as those in the first embodiment are denoted by the same reference numerals.

The second embodiment is similar to the first embodiment except that configurations of the nozzle unit 2A and the control unit 6A are different.

The nozzle unit 2A shown in FIGS. 6 and 7 further includes a second vibration applying unit 82.

That is, a liquid ejection device 1A according to the present embodiment includes the second vibration applying unit 82 that applies vibration to the nozzle 22. In particular, the second vibration applying unit 82 is provided between the nozzle 22 and the suction tube 28 in FIGS. 6 and 7. The second vibration applying unit 82 may apply vibration to the liquid conveying tube 24. In this case, the second vibration applying unit 82 may be provided between the liquid conveying tube 24 and the suction tube 28. Similar to the first vibration applying unit 81, the second vibration applying unit 82 applies vibration to the nozzle 22 or the liquid conveying tube 24. Compared with the first embodiment, patterns generated when the vibration is applied to the nozzle 22 or the liquid conveying tube 24 can be increased by providing such a second vibration applying unit 82. Accordingly, droplet formation of the ejected flow L1 can be further facilitated, and the droplet forming distance DD can be further shortened.

The second vibration applying unit 82 according to the present embodiment has the same configuration as the first vibration applying unit 81 according to the first embodiment. For example, the second vibration applying unit 82 according to the present embodiment includes a piezoelectric element 821. A wire 295 is drawn out from the piezoelectric element 821 via the suction tube 28. The piezoelectric element 821 is electrically coupled to the control unit 6A via the wire 295. The piezoelectric element 821 vibrates so as to repeatedly expand and contract along the Z axis, based on an inverse piezoelectric effect, according to a second drive signal S2 output from the control unit 6A.

The piezoelectric element 821 can be replaced with any element or mechanical element described above.

The control unit 6A according to the present embodiment further includes a second vibration applying control unit 65.

The second vibration applying control unit 65 outputs the second drive signal S2 to the second vibration applying unit 82. Drive of the piezoelectric element 821 is controlled by the second drive signal S2.

An example of a control performed by the control unit 6A includes a control of making at least one of a frequency, an amplitude, a phase, and a waveform different by using the first drive signal S1 and the second drive signal S2. As compared with the first embodiment, the vibration can be applied to the nozzle 22 or the liquid conveying tube 24 in more diversified patterns under such a control.

A position of the first vibration applying unit 81 and a position of the second vibration applying unit 82 shown in FIG. 7 are different from each other in a direction of an axis A1 of the liquid conveying tube 24. That is, the first vibration applying unit 81 and the second vibration applying unit 82 shown in FIG. 7 are arranged along the axis A1.

The first vibration applying unit 81 and the second vibration applying unit 82 vibrate in an X-Z plane by adopting such an arrangement. Therefore, the ejected flow L1 can be vibrated at various patterns in the X-Z plane. Accordingly, the droplet forming distance DD can be further shortened.

A drive frequency of the second vibration applying unit 82 is not particularly limited, and is preferably 0.01 kHz or more and 50 kHz or less, and more preferably 0.5 kHz or more and 30 kHz or less. Accordingly, the droplet forming distance DD can be further shortened, and the droplets L2 can be generated more stably.

A voltage of the second drive signal S2 input into the second vibration applying unit 82 slightly varies depending on a configuration of the piezoelectric element 821, and is preferably 1 V or more and 100 V or less. Accordingly, since the piezoelectric element 821 vibrates at a necessary and sufficient amplitude, the droplets L2 can be generated more stably.

A waveform of the second drive signal S2 input into the second vibration applying unit 82 may be a periodic waveform such as a sine wave, a rectangular wave, and a sawtooth wave, a non-periodic waveform, or the like.

In the second embodiment described above, the same effects as the first embodiment can also be obtained.

3. Third Embodiment

Next, a liquid ejection device according to the third embodiment will be described.

Figure 8:
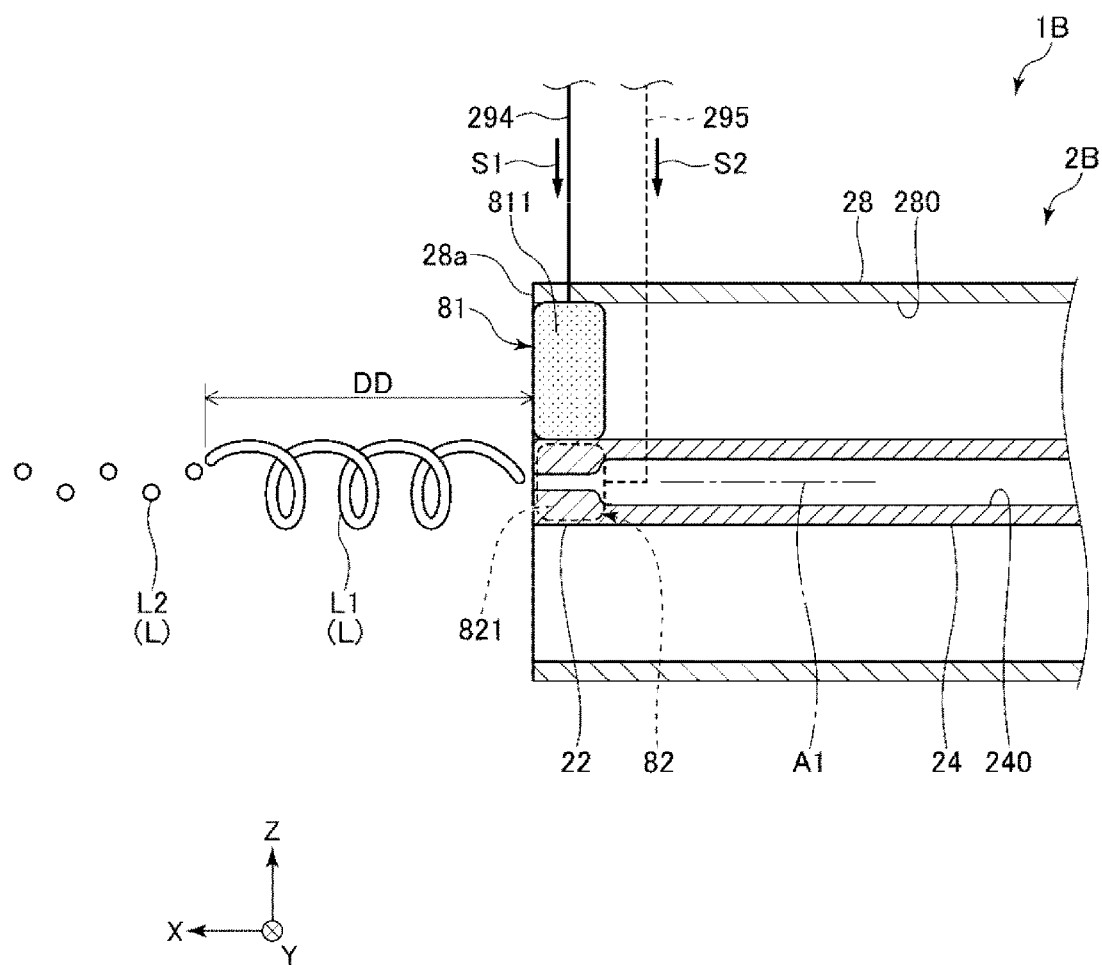
FIG. 8 is a cross-sectional view showing a nozzle unit of a liquid ejection device according to a third embodiment.
Figure 9:
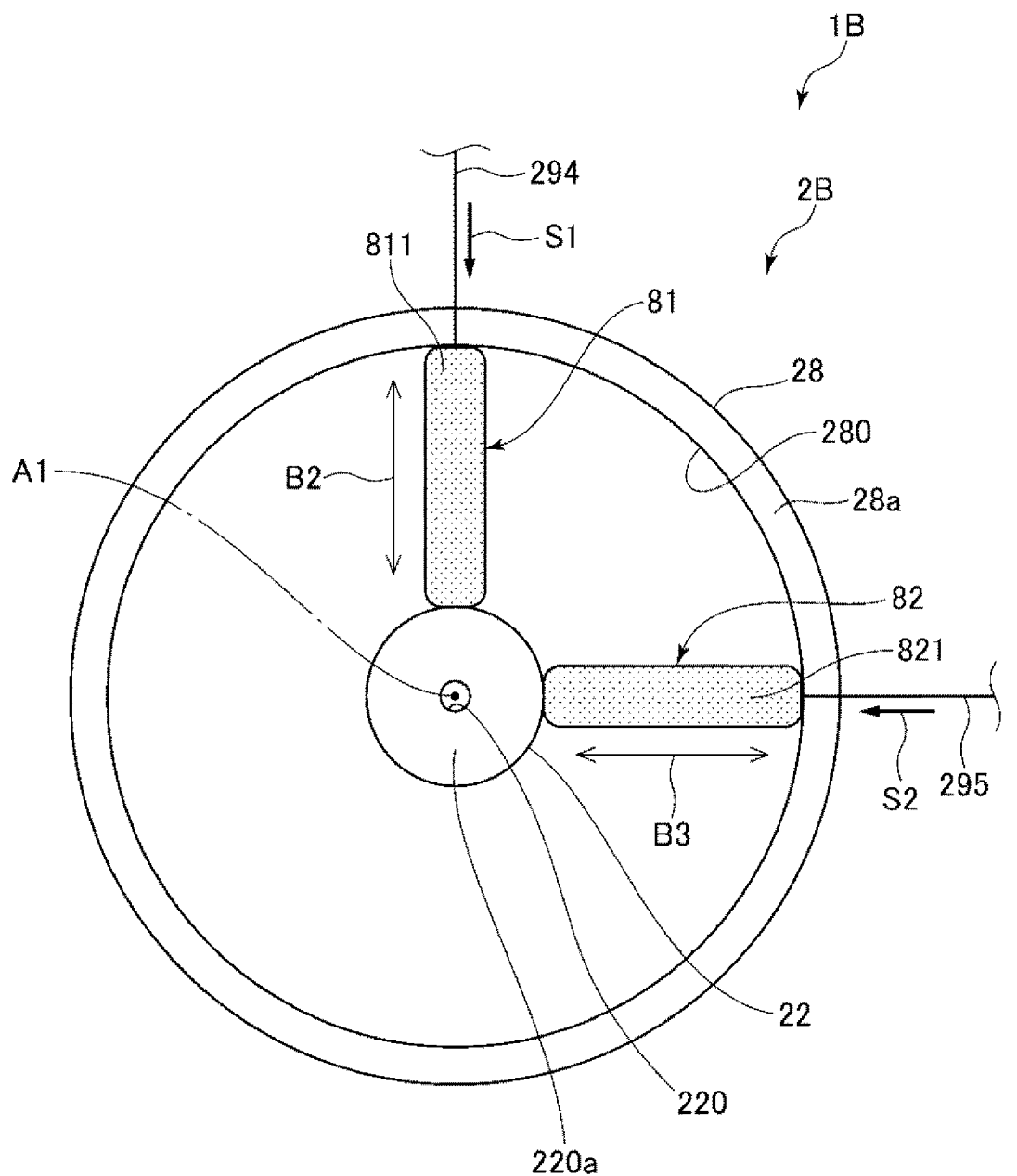
FIG. 9 is a view showing the nozzle unit of the liquid ejection device according to the third embodiment as viewed from a tip end side.

FIG. 8 is a cross-sectional view showing a nozzle unit of the liquid ejection device according to the third embodiment. FIG. 9 is a view showing the nozzle unit of the liquid ejection device according to the third embodiment as viewed from a tip end side.

Hereinafter, the third embodiment will be described, differences from the second embodiment will be mainly described in the following description, and descriptions of the same matters will be omitted. In FIGS. 8 and 9, the same components as those in the second embodiment are denoted by the same reference numerals.

The third embodiment is similar to the second embodiment except that a configuration of a nozzle unit 2B is different.

In the nozzle unit 2A according to the second embodiment described above, the first vibration applying unit 81 and the second vibration applying unit 82 are arranged along the X axis. In contrast, in the nozzle unit 2B according to the present embodiment, the first vibration applying unit 81 and the second vibration applying unit 82 are arranged such that the piezoelectric element 811 of the first vibration applying unit 81 vertically vibrates along the vibration axis B2 parallel to the Z axis and the piezoelectric element 821 of the second vibration applying unit 82 vertically vibrates along a vibration axis B3 parallel to the Y axis, as shown in FIGS. 8 and 9. Therefore, the ejected flow L1 is vibrated in a vibration pattern having no component along the Y axis in the nozzle unit 2A according to the second embodiment while the ejected flow L1 is vibrated in a vibration pattern having a component along three axes of the X axis, the Y axis, and the Z axis in the nozzle unit 2B according to the present embodiment. Therefore, the droplet forming distance DD can be further shortened according to the present embodiment. As a result, the liquid ejection device 1B having higher work efficiency can be implemented.

For example, from the control unit 6, a sine wave is output as the first drive signal S1, and a sine wave, whose frequency and amplitude are the same as the first drive signal S1 and whose phase is shifted by 90° from the first drive signal S1, is output as the second drive signal S2. Accordingly, the ejected flow L1 flies in a spiral manner as shown in FIG. 8. Therefore, it is more likely to change the ejected flow L1 to the droplets L2, and the droplet forming distance DD can be particularly shortened. A phase difference between the first drive signal S1 and the second drive signal S2 is not limited to 90°. The frequency and the amplitude of the second drive signal S2 may be different from the frequency and the amplitude of the first drive signal S1.

The ejected flow L1 flies in a spiral manner, so that a colliding range in which the droplets L2 collides with the work object W can be expanded to a wide range. As a result, the work region can be easily expanded to improve the work efficiency.

As described above, in a liquid ejection device 1B according to the present embodiment, the first vibration applying unit 81 generates vibration in a direction of the vibration axis B2 (a first axis) intersecting the axis A1 of the liquid conveying tube 24, and the second vibration applying unit 82 generates vibration in a direction of the vibration axis B3 (a second axis) that is different from the direction of the vibration axis B2 and intersects the axis A1 of the liquid conveying tube 24.

According to the liquid ejection device 1B, the droplet forming distance DD can be further shortened as described above. As a result, the liquid ejection device 1B having higher work efficiency can be implemented.

As shown in FIG. 9, the vibration axis B2 and the vibration axis B3 intersecting the axis A1 refers to that the vibration axis B2 and the vibration axis B3 may be not parallel to the X axis when the axis A1 is parallel to the X axis. However, the vibration axis B2 and the vibration axis B3 are preferably parallel to a Y-Z plane considering efficiency of applying vibration to the ejected flow L1. In the present specification, "parallel" is a concept including a state of a shift angle of 5° or less.

An angle between the vibration axis B2 and the vibration axis B3 is not particularly limited as long as the angle is larger than 0° and 180° or less. The angle is preferably 10° or more and 170° or less, and more preferably 60° or more and 120° or less. Accordingly, since the ejected flow L1 can fly in a spiral manner, droplet formation of the ejected flow L1 can be particularly facilitated. A shape of the spiral is not particularly limited. When viewed from the X axis positive side, an outer shape of the spiral may be a circle such as a perfect circle and an ellipse, or a polygon such as a square, a rectangle, a triangle, and a hexagon.

Similar to the second embodiment, when the first vibration applying unit 81 includes the piezoelectric element 811 and the second vibration applying unit 82 includes the piezoelectric element 821, the vibration pattern of the piezoelectric element 811 and the piezoelectric element 821 may be a periodic pattern or a non-periodic pattern as long as the vibration pattern can displace the nozzle 22 in any direction. When the vibration pattern is a periodic pattern, the frequency of the variation pattern may be constant or variable. The piezoelectric element 811 and the piezoelectric element 821 may be elements that expand and contract along the Z axis and the Y axis as shown in FIG. 9, or may be elements that expand and contract along other vibration axes. The piezoelectric element 811 and the piezoelectric element 821 may be a flexural vibration element.

According to the liquid ejection device 1B, when the liquid L is ejected from the nozzle unit 2B, the ejected flow L1 can fly in various trajectories as described above. Accordingly, the droplet forming distance DD can be further shortened.

As described above, the liquid ejection device 1B according to the present embodiment includes a control unit 6B that outputs the first drive signal S1 which is a periodic signal for controlling the drive of the first vibration applying unit 81 and the second drive signal S2 which is a periodic signal for controlling the drive of the second vibration applying unit 82. Phases of the first drive signal S1 and the second drive signal S2 are shifted from each other.

According to the liquid ejection device 1B, when the ejected flow L1 is ejected from the nozzle unit 2B, the ejected flow L1 can fly in a spiral manner as described above. Therefore, the droplet forming distance DD can be further shortened.

A liquid ejection device control method according to the present embodiment corresponds to a control performed by the control unit 6B. That is, the liquid ejection device control method according to the present embodiment is a method for controlling the liquid ejection device 1B including the nozzle 22 that ejects the liquid L, the liquid conveying tube 24 that conveys the liquid L to the nozzle 22, the first vibration applying unit 81 that generates vertical vibration (first periodic vibration) along the vibration axis B2 in the nozzle 22 or the liquid conveying tube 24, and the second vibration applying unit 82 that generates vertical vibration (second periodic vibration) along the vibration axis B3 in the nozzle 22 or the liquid conveying tube 24. The control method includes ejecting the liquid L from the nozzle 22, and generating the first periodic vibration and the second periodic vibration having phases shifted from each other by the first vibration applying unit 81 and the second vibration applying unit 82.

According to such a control method, the ejected flow L1 flying from the nozzle 22 can fly in a spiral manner by, for example, optimizing a phase shift between the first periodic vibration and the second periodic vibration. Accordingly, the droplet forming distance DD can be further shortened. In addition, the first vibration applying unit 81 and the second vibration applying unit 82 are likely to have a relatively small size. Therefore, the liquid ejection device 1B having a small size can be implemented, and the work can be efficiently performed using the liquid ejection device 1B.

In the third embodiment described above, the same effects as the second embodiment can also be obtained.

4. Fourth Embodiment

Next, a liquid ejection device according to the fourth embodiment will be described.

Figure 10:
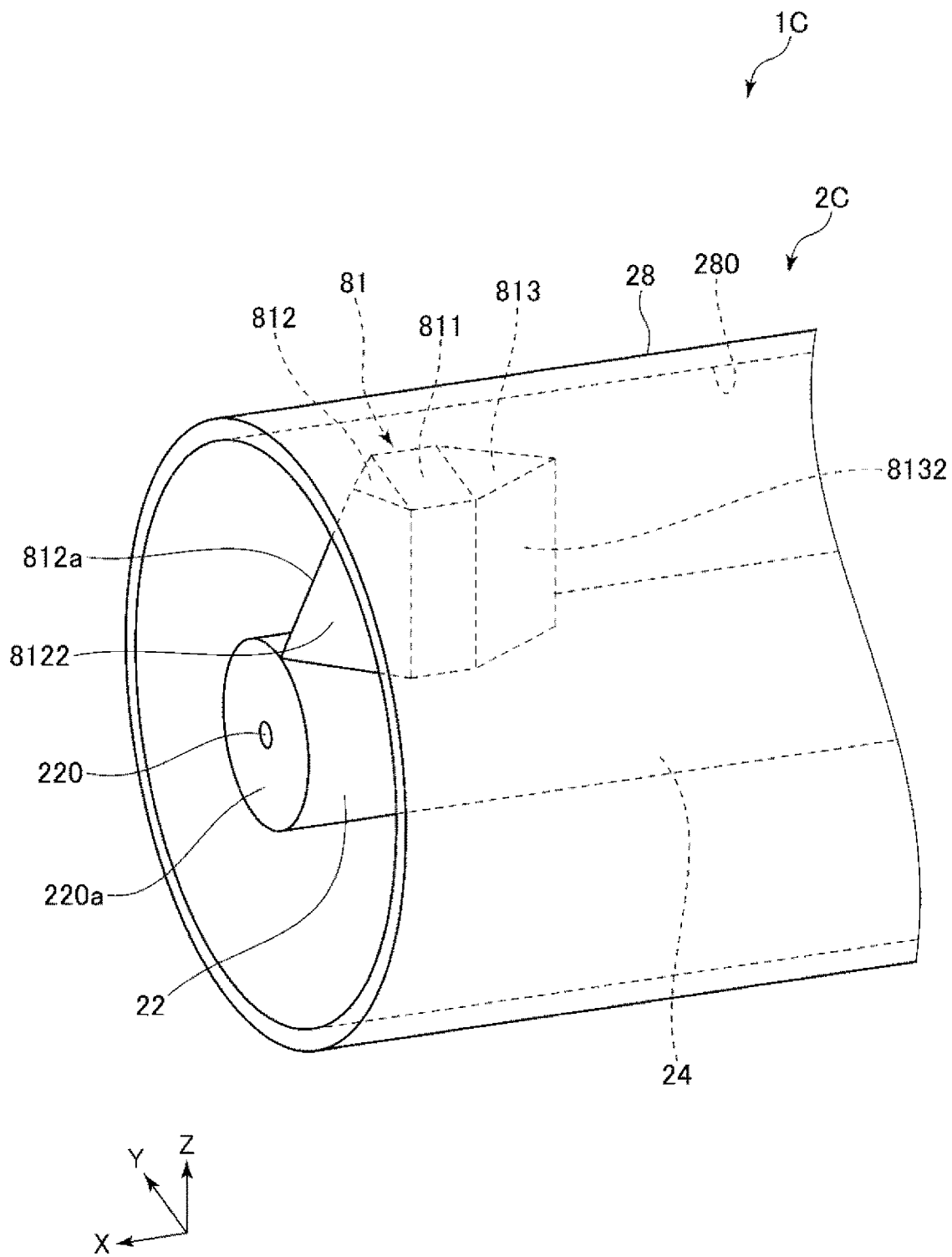
FIG. 10 is a partial perspective view showing a nozzle unit of a liquid ejection device according to a fourth embodiment.
Figure 11:
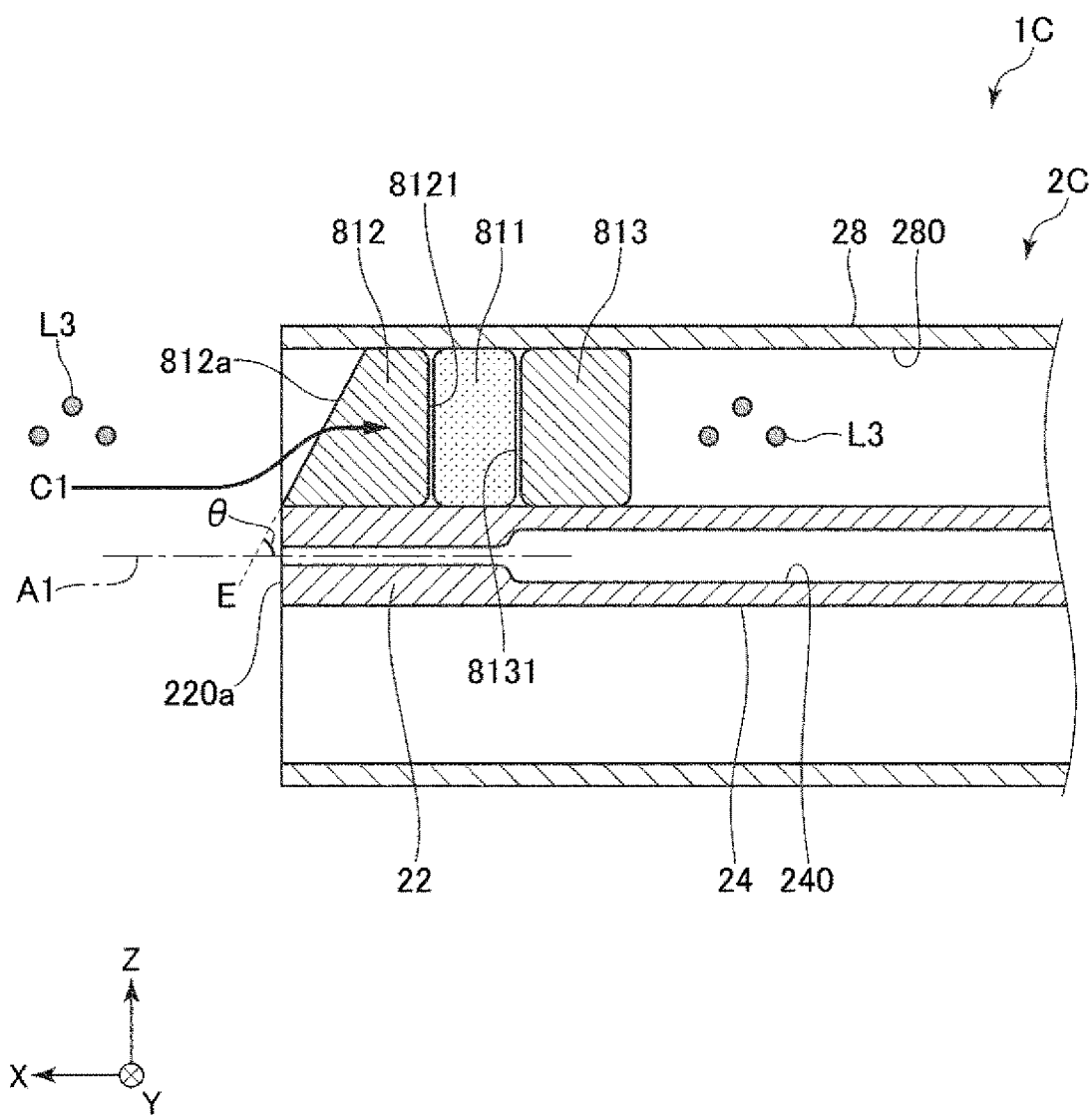
FIG. 11 is a cross-sectional view showing the nozzle unit shown in FIG. 10.
Figure 12:
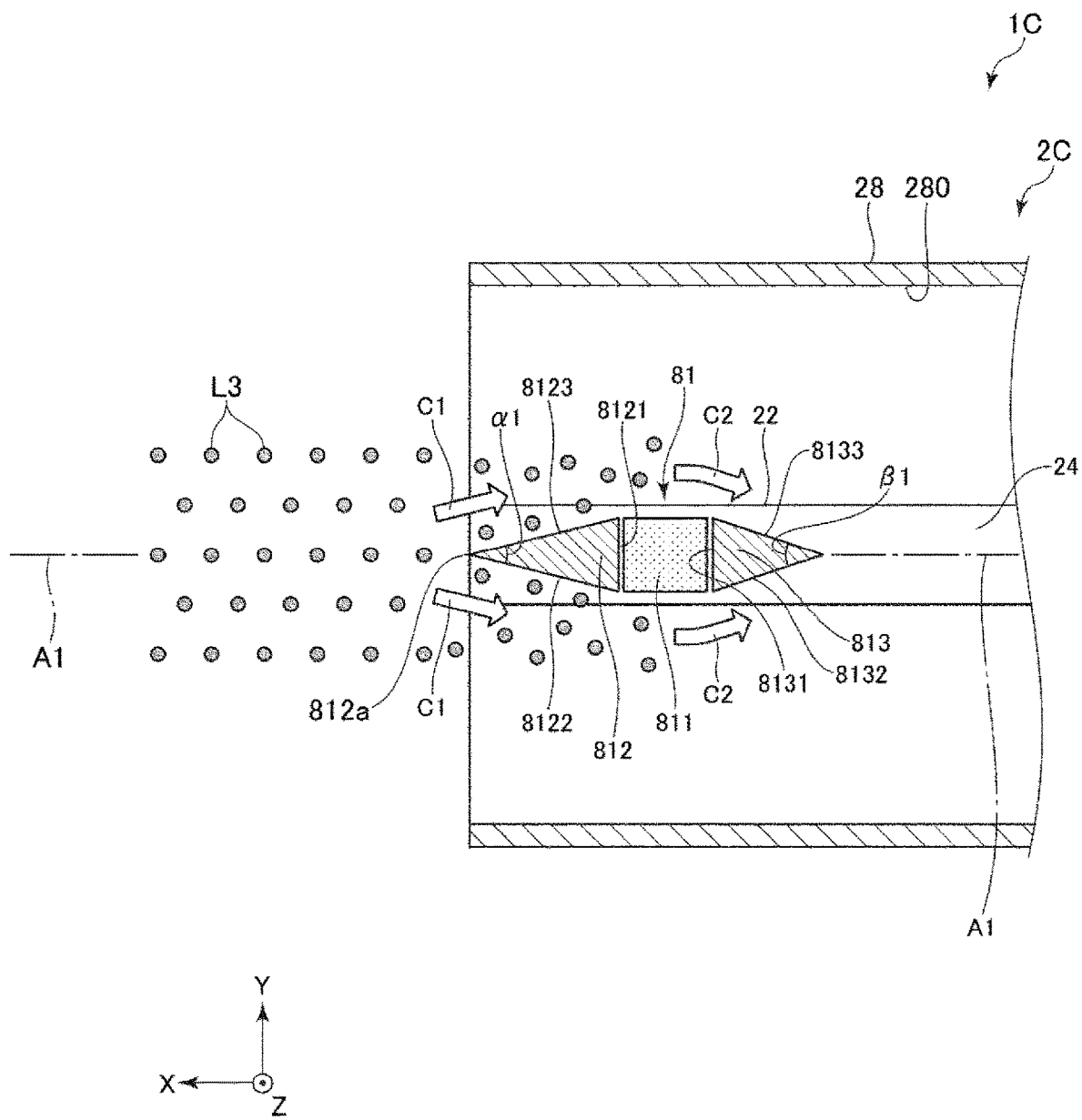
FIG. 12 is a cross-sectional view showing portions of the nozzle unit different from those of the nozzle unit shown in FIG. 11.

FIG. 10 is a partial perspective view showing a nozzle unit of the liquid ejection device according to the fourth embodiment. FIG. 11 is a cross-sectional view showing the nozzle unit shown in FIG. 10. FIG. 12 is a cross-sectional view showing portions of the nozzle unit different from those of the nozzle unit shown in FIG. 11.

Hereinafter, the fourth embodiment will be described, differences from the first embodiment will be mainly described in the following description, and the description of the same matters will be omitted. In FIGS. 10 to 12, the same components as those in the first embodiment are denoted by the same reference numerals.

A liquid ejection device 1C according to the fourth embodiment is the same as the liquid ejection device 1 according to the first embodiment except that a configuration of a nozzle unit 2C is different.

In the nozzle unit 2C according to the present embodiment, the first vibration applying unit 81 includes a first rectification unit 812 (member) and a second rectification unit 813 in addition to the piezoelectric element 811.

The first rectification unit 812 is provided between the nozzle 22 and the suction tube 28 or between the liquid conveying tube 24 and the suction tube 28. The first rectification unit 812 is provided adjacent to a tip end side of the piezoelectric element 811. The first rectification unit 812 has a shape of a truncated triangular pyramid having an axis parallel to the Z axis. The first rectification unit 812 has three side surfaces 8121, 8122, and 8123. As shown in FIGS. 11 and 12, the side surface 8121 is provided at a position having a small gap from the piezoelectric element 811. Accordingly, the first rectification unit 812 is less likely to affect the drive of the piezoelectric element 811.

On the other hand, the second rectification unit 813 is also provided between the nozzle 22 and the suction tube 28 or between the liquid conveying tube 24 and the suction tube 28. The second rectification unit 813 is provided adjacent to a base end side of the piezoelectric element 811. The second rectification unit 813 has a shape of a triangular prism having an axis parallel to the Z axis. The second rectification unit 813 has three side surfaces 8131, 8132, and 8133. As shown in FIGS. 11 and 12, the side surface 8131 is provided in contact with the piezoelectric element 811 or is provided at a position having a small gap from the piezoelectric element 811. Accordingly, the second rectification unit 813 is less likely to affect the drive of the piezoelectric element 811.

The side surfaces 8122 and 8123 of the first rectification unit 812 are separately parallel to planes obtained by slightly rotating an X-Z plane around the Z axis. When the first rectification unit 812 is viewed from the Z axis positive side, as shown in FIG. 12, the side surface 8122 is positioned at the Y axis negative side than the axis A1 of the liquid conveying tube 24, and the side surface 8123 is positioned at the Y axis positive side than the axis A1.

The side surfaces 8122 and 8123 provided at the positions as described above rectify an airflow C1 flowing towards the suction channel 280 of the suction tube 28 to divide the airflow C1 into two airflows as shown in FIG. 12. Since the discharged liquid L3 is suctioned along the airflow C1, even when a foreign matter or the like is mixed in the discharged liquid L3, the foreign matter is less likely to be caught by the first vibration applying unit 81. Therefore, the time and effort for removing the foreign matter can be reduced.

An angle $\alpha 1$ between the side surface 8122 and the side surface 8123 is not particularly limited, and is preferably 70° or less, and more preferably 5° or more and 60° or less. Accordingly, a resistance generated when the first rectification unit 812 suctions the discharged liquid L3 can be reduced, and a size of the side surface 8121 enough to cover the piezoelectric element 811 can be ensured.

Similarly, the side surfaces 8132 and 8133 of the second rectification unit 813 are also separately parallel to planes obtained by slightly rotating the X-Z plane around the Z axis. When the second rectification unit 813 is viewed from the Z axis positive side, as shown in FIG. 12, the side surface 8132 is positioned at the Y axis negative side than the axis A1 of the liquid conveying tube 24, and the side surface 8133 is positioned at the Y axis positive side than the axis A1.

The side surfaces 8132 and 8133 provided at the positions as described above have a function of bending two airflows C2 generated in the vicinity of the piezoelectric element 811 in a direction of combining the two airflows C2 into one airflow again, as shown in FIG. 12. Accordingly, an airflow vortex is less likely to occur at the base end side of the piezoelectric element 811. If an airflow vortex occurs, it is likely to stagnate a foreign matter or the like in the airflow vortex. The time and effort for removing the foreign matter can be reduced by preventing the airflow vortex from occurring.

The second rectification unit 813 may be provided as needed, and may be omitted depending on a shape of the piezoelectric element 811.

An angle $\beta 1$ between the side surface 8132 and the side surface 8133 is not particularly limited, and is preferably 70° or less, and more preferably 5° or more and 60° or less. Accordingly, the airflow vortex can be reliably prevented from occurring, and a size of the side surface 8131 enough to cover the piezoelectric element 811 can be ensured.

A ridge line 812a is formed between the side surface 8122 and the side surface 8123 of the first rectification unit 812. The ridge line 812a may be orthogonal to the axis A1 of the liquid conveying tube 24. However, the ridge line 812a is inclined in the present embodiment. Specifically, an extension line E of the ridge line 812a may be perpendicular to the axis A1. However, the extension line E intersects the axis A1 at an acute angle $\theta$ in FIG. 11. In the present specification, intersection of the extension line E of the ridge line 812a with the axis A1 is simply referred to as intersection of the ridge line 812a and the axis A1. The angle $\theta$ is an angle formed between the extension line E and the axis A1 at a first rectification unit 812 side.

That is, the first vibration applying unit 81 according to the present embodiment includes the first rectification unit 812 (member), and the first rectification unit 812 has the ridge line 812a intersecting a direction of the axis A1 of the liquid conveying tube 24 at an acute angle.

When such a first rectification unit 812 is provided, as shown in FIG. 11, the airflow C1 can be bent in a direction away from the axis A1 towards the Z axis positive side at a tip end side of the nozzle opening 220a. The airflow C1 can guide the discharged liquid L3 to be away from the tip end side of the nozzle opening 220a. Accordingly, the ejected flow L1 ejected from the nozzle 22 and the droplets L2 can be prevented from being affected by the discharged liquid L3. In addition, when such a ridge line 812a is provided, even if a foreign matter is caught by the ridge line 812a, the caught foreign matter is likely to move to the Z axis positive side. Therefore, the airflow C1 in the vicinity of the nozzle 22 can be prevented from being disordered by the foreign matter.

The angle $\theta$ may be an acute angle, and is, for example, preferably less than 90°, more preferably 10° or more and 85° or less, and even more preferably 20° or more and 80° or less. Accordingly, the effects described above are more significant.

The ridge line 812a may be rounded. That is, the side surface 8122 and the side surface 8123 may be coupled by a curved surface.

Constituent materials of the first rectification unit 812 and the second rectification unit 813 are not particularly limited, and examples of the constitution materials include a metal material, a ceramic material, a glass material, and a resin material. Alternatively, the constitution material may be a composite material containing at least one of these materials.

A foreign matter may be inevitably caught in the first rectification unit 812 and the second rectification unit 813. In such a case, the foreign matter may be crushed or peeled off by driving the piezoelectric element 811. In this case, a drive mode of the piezoelectric element 811 may be changed to a mode different from a normal mode. Similarly, a drive mode of the suction pump 76 may be changed to a mode different from a normal mode. Then, the foreign matter can be efficiently removed by alternately repeating vibration application to the foreign matter by the piezoelectric element 811 and suction of the foreign matter by the suction pump 76.

Although the liquid ejection device and the liquid ejection device control method according to the present disclosure have been described above based on the illustrated embodiments, the present disclosure is not limited to the embodiments.

For example, in the liquid ejection device according to the present disclosure, a configuration of each unit in the embodiments may be replaced with any configuration having the same function, and any configuration may be added to the configuration in the embodiments.

An arrangement of the first vibration applying unit and the second vibration applying unit is not limited to the positions described above, and the first vibration applying unit and the second vibration applying unit may be provided at any position as long as the first vibration applying unit and the second vibration applying unit are provided between the nozzle and the outer tube or between the liquid conveying tube and the outer tube. The liquid ejection device according to the present disclosure may be used by combining two or more of the above-described embodiments.

In addition to the first vibration applying unit and the second vibration applying unit, the nozzle unit may include three or more vibration applying units.

What is claimed is:

1. A liquid ejection device comprising:
a liquid feeding pump configured to supply a liquid to a nozzle at a predetermined pressure, the liquid feeding pump being connected to a liquid supplying tube
a liquid conveying tube connected to the liquid supplying tube and configured to convey the liquid from the liquid feeding pump to the nozzle, the nozzle being provided at an end of the liquid conveying tube, the nozzle being configured to eject the liquid therefrom to an outside as an ejected liquid flow;
an outer tube that is internally provided with the nozzle and the liquid conveying tube, the outer tube having a suction channel therein, the suction channel circumscribing the liquid conveying tube, the suction channel being connected to a suction pump via a suction tube; and
a second piezoelectric device configured to apply vibration to the nozzle or the liquid conveying tube so as to transfer the vibration to the ejected liquid flow, wherein
a first piezoelectric device disposed directly adjacent to the nozzle, the first piezoelectric device being configured to apply vibration to the nozzle and the liquid conveying tube so as to transfer the vibration to the ejected liquid flow, wherein
the first piezoelectric device spans between an inner surface of the outer tube and one of an outer surface of the nozzle or an outer surface of the liquid conveying tube,
the suction channel is configured to suck part of the liquid of the ejected liquid flow,
the first piezoelectric device is configured to generate the vibration in a first axial direction intersecting an axis of the liquid conveying tube, and
the second piezoelectric device is configured to generate the vibration in a second axial direction intersecting the axis of the liquid conveying tube and different from the first axial direction.

2. The liquid ejection device according to claim 1, wherein
an internal pressure of the outer tube is lower than an atmospheric pressure.

3. The liquid ejection device according to claim 1, wherein
the first piezoelectric device includes a member having a ridge line intersecting an axis direction of the liquid conveying tube at an acute angle.

4. The liquid ejection device according to claim 1, wherein
a position of the first piezoelectric device is different from a position of the second piezoelectric device in an axis direction of the liquid conveying tube.

5. The liquid ejection device according to claim 1, further comprising:
a controller configured to output a first drive signal which is a periodic signal for controlling drive of the first piezoelectric device and a second drive signal which is a periodic signal for controlling drive of the second piezoelectric device, wherein
a phase of the first drive signal is shifted from a phase of the second drive signal.

6. The liquid ejection device according to claim 1, wherein
an inner diameter of the suction channel is 2 times or more and 20 times or less than an inner diameter of the nozzle or the liquid conveying tube.

\* \* \* \* \*